United States Patent [19]

Koppitsch et al.

[11] Patent Number: 4,843,327

[45] Date of Patent: Jun. 27, 1989

[54] BRANCHED SENSOR SYSTEM

[75] Inventors: Heinrich Koppitsch, Menlo Park; Francis C. Sparling, Sunnyvale, both of Calif.

[73] Assignee: Raychem Corporation, Menlo Park, Calif.

[21] Appl. No.: 57,459

[22] Filed: Jun. 3, 1987

[51] Int. Cl.[4] ............................................. G01R 31/08
[52] U.S. Cl. ................................. 324/525; 174/11 R; 324/512; 324/65 R; 340/602; 379/26
[58] Field of Search ............ 324/525, 512, 509, 65 R; 379/331, 26; 361/58, 42, 49; 340/602; 338/38; 174/11 R

[56] References Cited

U.S. PATENT DOCUMENTS

| | | | |
|---|---|---|---|
| 3,234,459 | 2/1966 | Brazee | 324/525 X |
| 3,248,646 | 4/1966 | Brazee | 324/525 X |
| 3,460,123 | 8/1969 | Bass | 340/602 X |
| 3,560,850 | 2/1971 | Hojding | 324/52 |
| 3,668,472 | 6/1972 | Shields et al. | 361/49 |
| 4,013,924 | 3/1977 | Christensen et al. | 361/49 |
| 4,442,422 | 4/1984 | Murata et al. | 73/29 X |

FOREIGN PATENT DOCUMENTS 0133748 3/1985 European Pat. Off. .
0160440 6/1985 European Pat. Off. .
0160441 6/1985 European Pat. Off. .

*Primary Examiner*—Reinhard J. Eisenzopf
*Assistant Examiner*—Robert W. Mueller
*Attorney, Agent, or Firm*—Timothy H. P. Richardson; Herbert G. Burkard

[57] ABSTRACT

A detection and location system, e.g. liquid leaks, comprising a trunk line sensor cable and at least one branch line cable; each of the cables comprise two insulated conductors and two non-insulated conductors which are not connected to each other in the absence of a leak but which become connected upon occurrence of a leak. In the trunk line cable, the insulated conductors form part of a circuit which enables the location of a leak to be detected. In the branch line, one of the insulated conductors and one of the non-insulated conductors are connected so as to form a loop connecting the ends of the non-insulated conductors of the branch cable.

16 Claims, 2 Drawing Sheets

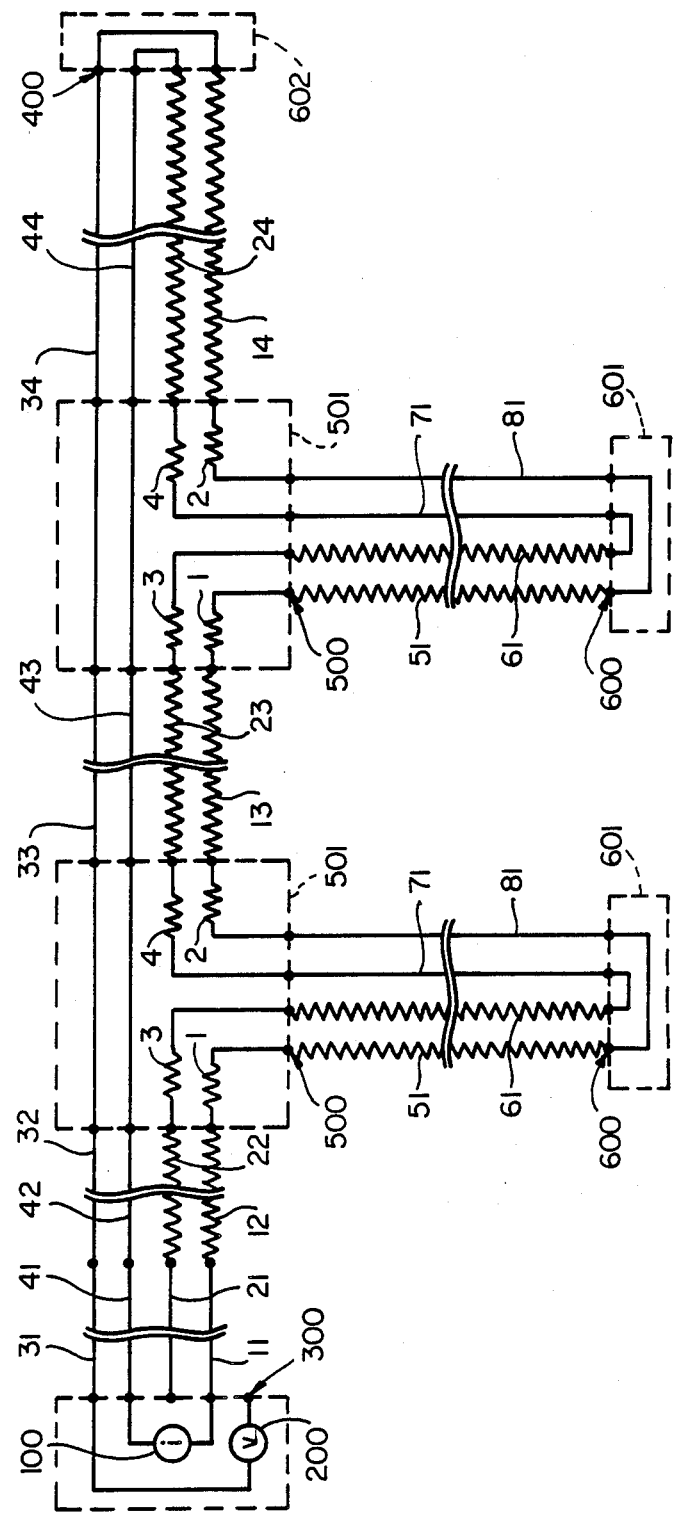
FIG_1

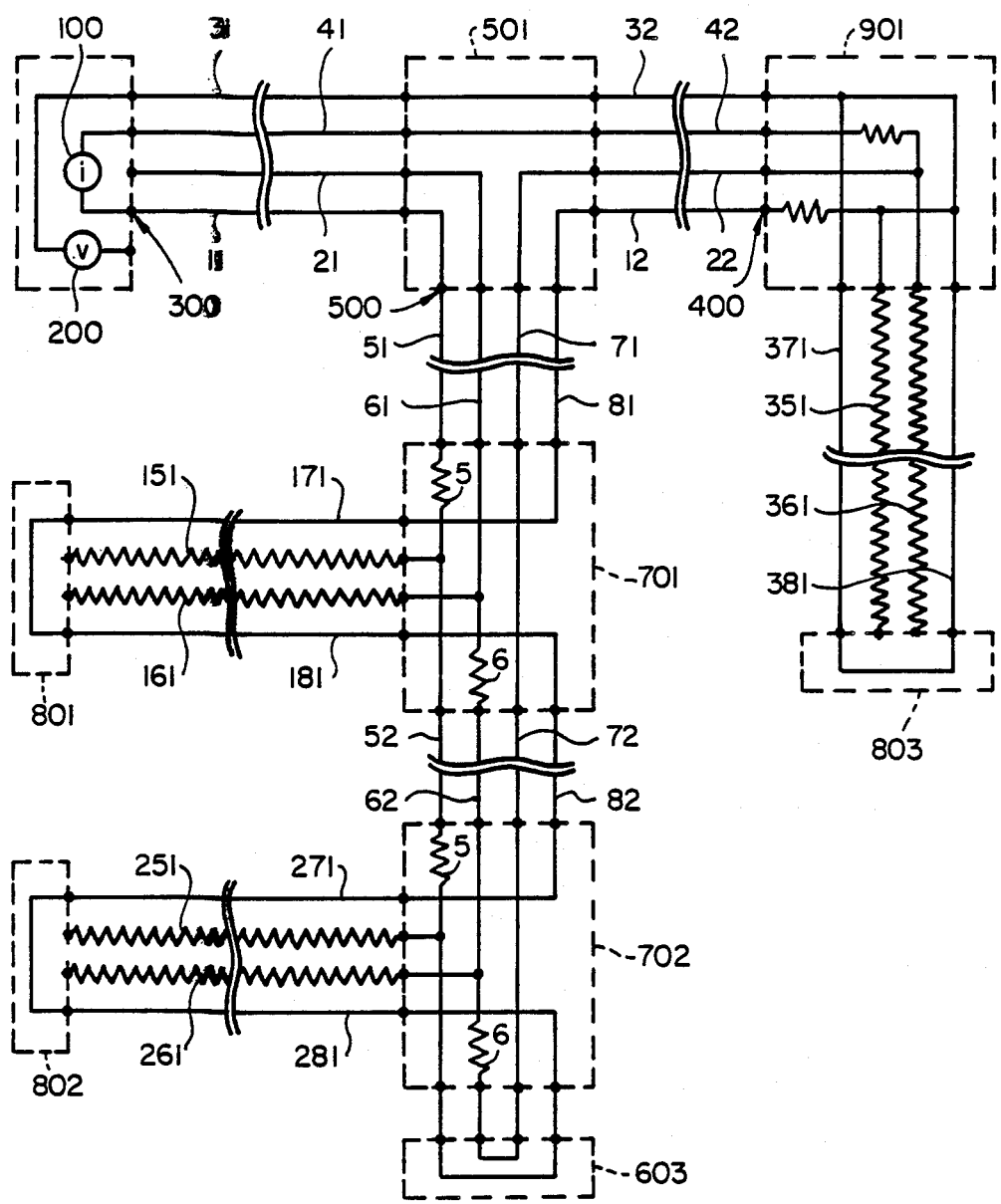
FIG_2

BRANCHED SENSOR SYSTEM

BACKGROUND OF THE INVENTION

1. Field of the Invention

This invention relates to methods and apparatus for detecting and locating changes in variables.

2. Introduction to the Invention

Copending commonly assigned U.S. Application Ser. Nos. 832,562 filed Feb. 20, 1986, 831,758 filed Feb. 20, 1986, now abandoned in favor of continuation-in-part application Ser. No. 017,375, and 838,725 filed Mar. 11, 1986, the entire disclosures of which are incorporated herein by reference, disclose methods and apparatus for detecting and obtaining information about (particularly locating) changes in variables. Such changes are referred to in that application, and likewise in this application, by the generic term "event". In a preferred embodiment disclosed in Ser. No. 832,562 (and also disclosed in Ser. No. 618,109, filed June 7, 1984, now abandoned, of which Ser. No. 832,562 is a continuation-inpart), the apparatus comprises a sensor cable comprising two insulated wires and two "non-insulated" wires which are not connected to each other in the absence of an event but which become electrically connected to each other upon occurrence of an event. The non-insulated wires can for example comprise a metal core surrounded by a conductive polymer jacket, so that the wires become electrically connected if there is a water leak. The term "conductive polymer" is used herein to denote a composition which comprises a polymeric component (e.g. a thermoplastic, or an elastomer, or a mixture of two or more such polymers) and, dispersed in the polymeric component, a particulate conductive filler (e.g. carbon black, graphite, a metal powder, or two or more of these). The possibility of connection can for example exist at all points along an elongate path or over selected stretches or discrete locations of an elongate path; for example the non-insulated wires can be wires which are insulated except at spaced locations at each of which they can become connected through a switch which is switched on by occurrence of an event at the location of that switch.

When a four-wire sensor cable of the kind just described is used to detect events along one or more branch paths extending from a main (or trunk) path, the cable can simply be routed along the branch path to the end of the branch path and then back again to continue down the trunk path. However, this can lead to misleading results as to the location of the event, since an event taking place along the branch can cause connection of the non-insulated wires in both the outgoing branch cable and the incoming branch cable. This problem can be overcome by running the sensor cable from the junction of the trunk and branch paths to the end of the branch path only, and using four insulated "jumper" wires to make the appropriate connections from the end of the branch back to the trunk; but this is an expensive and inconvenient solution, especially when space is limited, eg. in a double containment system.

SUMMARY OF THE INVENTION

We have now recognised that in a branched system using a four-wire sensor cable, the two insulated wires are not needed in the branch line to perform the functions for which they are needed when the four wire sensor cable is part of a trunk line, and that these insulated wires can, therefore, be used as insulated jumper wires to connect the non-insulated wires between the junction of a branch and the end of a branch. Thus the insulated wires of the trunk cable which form the "return" and "auxiliary" members can simply be connected to each other across the junction; the non-insulated wires of the branch can be connected (a) at the junction, to the non-insulated wires coming into (or going out of) the junction along the trunk path, and (b) at the end of the branch, to the insulated wires of the branch; and the insulated wires of the branch can be connected at the junction to the non-insulated wires going out of (or coming into) the junction along the trunk path. In this way the errors which can occur with a simple loop system are substantially reduced or eliminated, as is the expense of the return leg of the four-wire sensor cable, or the inconvenience and expense of using separate jumper wires. Furthermore, the connections which have to be made at the end of the branch line can be the same as those made at the end of the trunk line, so that the same termination apparatus can be used.

Accordingly, in one aspect, the present invention provides an apparatus suitable for use in detecting and obtaining information about an event, the apparatus comprising (A) a power source;
(B) a voltage measuring device;
(C) a trunk line cable which follows an elongate trunk path having a near end and a far end; and
(D) at least one branch line cable which extends from the trunk line cable at an intermediate point along the trunk path and follows an elongate branch path from the intermediate point to a distant point;

the trunk line cable comprising first, second, third and fourth elongate electrically conductive members which, at least in the absence of an event, are insulated from each other along the length of the cable;

the branch line cable comprising fifth, sixth, seventh and eighth elongate electrically conductive members which, in the absence of an event, are insulated from each other along the length of the cable, the fifth and sixth members being such that there are locations along the branch line cable at which, upon occurrence of an event, the fifth and sixth members become electrically connected;

the first member being electrically connected (a) at the near end of the trunk path, to the power source and to the voltage-measuring device, and (b) at the far end of the trunk path, to the third member;

the third member being electrically connected (a) at the near end of the trunk path, to the voltage-measuring device, and (b) at the far end of the trunk path, to the first member;

the fourth member being electrically connected (a) at the near end of the trunk path, to the power source, and (b) at the far end of the trunk path, to the second member;

the first and second members being discontinuous at the intermediate point so that each has an incoming end nearer the near end of the trunk path and an outgoing end nearer the far end of the trunk path;

each of the fifth, sixth, seventh and eighth members being connected at the intermediate point to one of the incoming and outgoing ends of the first and second members, the fifth member being connected at the distant point of the branch line to the seventh or eighth member, and the sixth member being connected at the distant point of the branch line to the eighth member if the fifth member is connected to the seventh member and to the seventh member if the fifth member is connected to the eighth member, so that the incoming and outgoing ends of the first member are electrically connected to each other through the branch line, the incoming and outgoing ends of the second member are electrically connected to each other through the branch line, and, in the absence of an event, the first and second members are insulated from each other;

the second member and the members of the branch cable connected between the incoming and outgoing ends of the second member together forming a source member;

the first member and the members of the branch cable connected between the incoming and outgoing ends of the first member together forming a locating member which is insulated from the source member in the absence of an event but which, upon occurrence of an event, becomes electrically connected to the source member at a connection point, which has an impedance $Z_{total}$ between the near end and the far end of the trunk path, and whose impedance between the near end of the trunk path and any point on the locating member to which the source member can be connected upon occurrence of an event is characteristic of the event;

the apparatus being such that, when an event causes the locating member and the source member to become electrically connected to each other at a connection point, the apparatus comprises a test circuit and a reference circuit, the test circuit being one in which a current of known size flows and which comprises (a) that part of the locating member which lies between the near end of the trunk path and the connection point, (b) the connection, (c) that part of the source member which lies between the connection point and the far end of the trunk path, said part of the source member having an impedance which is substantially equal to the difference between $Z_{total}$ and the impedance of said part (a), (d) the fourth member of the trunk cable, and (e) the power source, and the reference circuit being one which comprises (a) the locating member, (b) the third member, and (c) the voltage-measuring device;

whereby the voltage measured by the voltage-measuring device can be used to determine the location of the connection point.

BRIEF DESCRIPTION OF THE DRAWING

The invention is illustrated in the accompanying drawing in which

FIGS. 1 and 2 are circuit diagrams of the apparatus of the invention.

DETAILED DESCRIPTION OF THE INVENTION

The trunk line cable comprises first, second, third and fourth elongate electrically conductive members. For any segments of the trunk line along which detection of an event is not required, the cable can simply comprise four insulated wires which are of low resistance. For any extended segments along which detection of an event is required, the trunk cable can comprise two low resistance insulated wires and two high resistance conductive-polymer-coated wires which become electrically connected to each other if an event occurs, eg. a leak of water or another electrolyte, or a leak of a hydrocarbon or other organic fluid which causes swelling of a component in the cable, thus effecting electrical connection; the high resistance wires are preferably identical and have a resistance per unit length which is substantially invariable under the operating conditions. The trunk cable can also comprise spaced-apart locations at which connection between the source and locating members takes place upon occurrence of an event, eg. through the operation of switch. One form of switch is a pair of conductive-polymer-coated wires which extend from the trunk cable; one wire is connected to the source member and the other to the locating member. The pair of wires can be part of a zone cable which extends from the trunk cable and which comprises in addition two insulated low resistance wires which are connected as a loop to form part of the return member and thus enable the continuity of the system to be checked. Other possible features of the branch line cable are described in the copending applications incorporated by reference.

The branch line cable can have the same characteristics as are described above for the trunk line cable, except that at least part of the branch line comprises members which, upon occurrence of an event, become electrically connected. However, the invention is particularly useful when the branch line cable comprises two low resistance insulated wires (which may be the same or different) and two conductive-polymer-coated wires (which are preferably the same), particularly when at least part of the trunk cable has substantially the same physical construction as the branch line cable. Particularly under such circumstances, it is preferred to put resistors in the connections between the conductive-polymer-coated wires; this results in discontinuities in the possible readings of the voltage-measuring device, so that despite a small error in the reading, the location of the event can be identified as being in the trunk line or branch line, as the case may be.

A very useful attribute of the apparatus of the present invention is that is can be assembled at an installation site from pre-terminated cables and preassembled connection and termination units which can be manufactured in a factory, thus eliminated the need to carry out in situ wiring, with the attendant risk of error. The various connection and termination units can be assembled (and if desired sealed) as flexible harnesses or in boxes.

Referring now to the drawing, in each of the Figures there is (A) a constant current power supply (100);

(B) a high impedance voltmeter (200);

(C) a trunk line cable which has a near end (300) and a far end (400), and which is made up of a plurality of segments, each segment comprising a first member (11, 12, 13 etc.), a second member (21, 22, 23 etc.), a third member (31, 32, 33 etc.) and a fourth member (41, 42, 43 etc.); and (D) at least one branch line cable which extends from an intermediate point (500) along the trunk path to a distant point (600) and which is made up of one or more segments, each segment comprising a fifth member (51, 52, 53 etc.), a sixth member (61, 62, 63 etc.), a seventh member (71, 72, 73 etc.) and an eighth member (81, 82, 83 etc.).

In each of the Figures, the phantom lines enclose components which can conveniently be preassembled in a manufacturing facility (eg. as a box or a flexible harness), with appropriate connecting means for the cables which make up the rest of the apparatus. The pre-assembled parts and the cables can then be assembled at the site of the installation.

Referring now to FIG. 1, this comprises a trunk cable having two identical branch cables connected thereto. The segment of the trunk cable closest to the near end 300 comprises four low resistance insulated wires 11, 21, 31 and 41 and extends along a path along which detection of an event is not required. The second, third and fourth segments of trunk cable comprise two low resistance insulated wires 32, 33 and 34, and 42, 43 and 44, and two identical high resistance conductive-polymer-coated wires 12, 13 and 14, and 22, 23 and 24 which become connected to each other if an event occurs, eg. a leak of water or a hydrocarbon. At each intermediate point 500, the trunk cable and the branch cable are connected to a preassembled T-connector 501 which will not detect occurrence of an event, which makes the connections shown, and which includes four identical resistors 1, 2, 3 and 4. The branch cable has a single segment which runs from the intermediate point 500 to the distant point 600 and which has the same physical construction as the second segment of the trunk cable and comprises two low resistance insulated wires 71 and 81 and two identical high resistance conductive-polymer-coated wires 51 and 61 which become connected to each other if an event occurs. At the distant point 600, the branch cable is connected to a preassembled terminator 601 which makes the connections shown. The final segment of the trunk cable is connected to a preassembled terminator 602 which makes the connections shown and which can be identical to terminator 601.

The wires 11, 12, 51 and 13, the resistors 1 and 2, and the connections between them together form a locating member. The wires 21, 22, 61 and 23, the resistors 3 and 4, and the connections between them together form a source member.

When the occurrence of an event causes a connection to be made at a single point along the trunk or branch cables (ie. between members 12 and 22, or members 51 and 61, or members 13 and 23), the voltage measured by the voltmeter depends upon the resistance of the locating member between the near end 300 and the connection point. Through knowledge of the resistance per unit length of the various components, or through prior mapping of the system, the measured voltage indicates the location of the event. The resistors 1, 2, 3 and 4 ensure that, despite a small error in the voltage measurement, an operator can distinguish between an event at an end of the trunk cable close to a T-connector and an event at the end of a branch cable close to a T-connector or at the end of a branch cable close to a terminator 601.

In FIG. 1, the connections in the T-connector are between members 51 and 12, 61 and 22, 71 and 23, and 81 and 13. However, since the members 71 and 81 have much lower resistance than the members 51 and 61, results which are substantially the same could be obtained by making the connections between 51 and 12 (as before), 81 and 13 (as before), 61 and 23, and 71 and 22; and results which are equally accurate, or substantially as accurate, but in which locations on the branch line were measured from the distant point instead of the intermediate point, could be obtained by making the connections between 12 and 71, 22 and 81, 51 and 23, and 61 and 13 (equally accurate) or between 12 and 71, 22 and 51, 81 and 23, and 61 and 13 (substantially as accurate).

FIG. 1 shows two branch lines, but there could be any number of branch lines.

Referring now to FIG. 2, this shows a system which will detect the occurrence of an event in one of a plurality of zones, but not elsewhere, and will identify the zone in which the event took place, but will not identify the location of the event in the zone. Between the zones, both the trunk cable and the branch cable comprise four insulated low resistance wires. In each zone, a first conductive-polymer-coated wire extends from the locating member, and a second conductive-polymer-coated wire extends from the source member, close to but not touching the first wire; upon occurrence of an event anywhere in the zone, the first and second wires are brought into electrical contact, thus connecting the source and locating members. Resistors are placed in the locating member so that the voltage measured by the voltmeter identifies the zone in which an event has taken place, and balancing resistors are placed in the source member.

The segment of the trunk cable closest to the near end 300 comprises four low resistance wires 11, 21, 31 and 41. At the intermediate point 500, the trunk cable and the branch cable are connected to a pre-assembled T-connector 501 which makes the connections shown. The first segment of the branch cable has the same physical construction as the trunk cable and contains four low resistance insulated wires, and is connected to a T-zone connector 701, which makes the connections shown between a zone cable and the first and second segments of the branch cable, and which contains resistors 5 and 6. The zone cable has the same physical construction as the branch cable of FIG. 1, and contains two low resistance insulated wires 171 and 181 and two conductive-polymer-coated wires 151 and 161. It is, however, connected differently both at the T-zone connector 701 and at the zone terminator 801; the wires 171 and 181 are connected as a loop between insulated wires 81 and 82 so that it is possible to make a continuity check of the zone cable. The second segment of the branch cable likewise contains four insulated wires 52, 62, 72 and 82. The second segment is connected to another T-zone connector 702 which is the same as 701 and to which is connected a second zone cable comprising insulated wires 271 and 281 and conductive- polymer-coated wires 251 and 261 and terminating in zone terminator 802. Terminator 603, which can be the same as terminator 601 used in FIG. 1 makes the appropriate connections at the end of the branch line.

The second segment of the trunk cable, comprising four insulated wires 12, 22, 32 and 42, is connected via an end zone connector 901 to a zone cable which is like that in the other zones, which comprises two insulated wires 371 and 381 and two conductive-polymer-coated wires 351 and 361, and which is connected to zone terminator 803.

We claim:

1. Apparatus suitable for use in detecting and obtaining information about an event, the apparatus comprising (A) a power source;
(B) a voltage measuring device; and
(C) an elongate sensor cable comprising
  (1) a trunk line cable which follows an elongate trunk path having a near end and a far end; and (2) at least one branch line cable which extends from the trunk line cable at an intermediate point along the trunk path and follows an elongate branch path from the intermediate point to a distant point;

the trunk line cable comprising first, second, third and fourth elongate electrically conductive members which, at least in the absence of an event, are insulated from each other along the length of the trunk line cable;

the branch line cable comprising fifth, sixth, seventh and eighth elongate electrically conductive members which, in the absence of an event, are insulated from each other along the length of the branch line cable, the fifth and sixth members being such that there are locations along the branch line cable at which, upon occurrence of an event, the fifth and sixth members become electrically connected;

the first member being electrically connected (a) at the near end of the trunk path, to the power source and to the voltage-measuring device, and (b) at the far end of the trunk path, to the third member;

the third member being electrically connected (a) at the near end of the trunk path, to the voltage-measuring device, and (b) at the far end of the trunk path, to the first member;

the fourth member being electrically connected (a) at the near end of the trunk path, to the power source, and (b) at the far end of the trunk path, to the second member;

the first and second members being discontinuous at the intermediate point so that each has an incoming end nearer the near end of the trunk path and an outgoing end nearer the far end of the trunk path;

each of the fifth, sixth, seventh and eighth members being connected at the intermediate point to one of the incoming and outgoing ends of the first and second members, the fifth member being connected at the distant point of the branch line cable to the seventh or eighth member, and the sixth member being connected at the distant point of the branch line cable to the eighth member if the fifth member is connected to the seventh member and to the seventh member if the fifth member is connected to the eighth member, so that the incoming and outgoing ends of the first member are electrically connected to each other through the branch line, the incoming and outgoing ends of the second member are electrically connected to each other through the branch line cable, and, in the absence of an event, the first and second members are insulated from each other along the length of the sensor cable;

the second member and the members of the branch line cable connected between the incoming and outgoing ends of the second member together forming a source member;

the first member and the members of the branch line cable connected between the incoming and outgoing ends of the first member together forming a locating member which is insulated from the source member along the length of the sensor cable in the absence of an event but which, upon occurrence of an event, becomes electrically connected to the source member at a connection point, which has an impedance $Z_{total}$ between the near end and the far end of the trunk path, and whose impedance between the near end of the trunk path and any point on the locating member to which the source member can be connected upon occurrence of an event is characteristic of the event;

the apparatus being such that, when an event causes the locating member and the source member to become electrically connected to each other at a connection point, the apparatus comprises a test circuit and a reference circuit, the test circuit being one in which a current of known size flows and which comprises
  (a) that part of the locating member which lies between the near end of the trunk path and the connection point,
  (b) the connection,
  (c) that part of the source member which lies between the connection point and the far end of the trunk path, said part of the source member having an impedance which is substantially equal to the difference between $T_{total}$ and the impedance of said part (a),
  (d) the fourth member of the trunk cable, and
  (e) the power source,
and the reference circuit being one which comprises
  (a) the locating member,
  (b) the third member, and
  (c) the voltage-measuring device;
whereby the voltage measured by the voltage-measuring device can be used to determine the location of the connection point.

2. Apparatus according to claim 1 wherein at least a part of the trunk cable comprises first and second members which are insulated from each other in the absence of an event but which become electrically connected to each other upon occurrence of an event.

3. Apparatus according to claim 2 wherein the physical construction of at least a part of the trunk cable is substantially identical to the physical construction of at least a part of the branch cable.

4. Apparatus according to claim 1 wherein the fifth member is connected, at the intermediate point, to the incoming end of the first member.

5. Apparatus according to claim 4 wherein the sixth member is connected, at the intermediate point, to the incoming end of the second member.

6. Apparatus according to claim 1 wherein the first, second, fifth and sixth members are substantially identical in physical construction.

7. Apparatus according to claim 6 wherein the third, fourth, seventh and eighth members are substantially identical in physical construction.

8. Apparatus according to claim 1 wherein at least a part of each of the first, second, fifth and sixth members comprises a metallic wire which is electrically surrounded by a conductive polymer composition which comprises a polymeric component and, dispersed in the polymeric component, a particulate conductive filler.

9. Apparatus according to claim 1 wherein a resistor is connected between each of the connections between the incoming and outgoing ends of the first and second members and the members of the branch cable to which they are respectively connected, the resistors being substantially identical.

10. Apparatus suitable for use in detecting and obtaining information about an event, the apparatus comprising
  (A) a power source;
  (B) a voltage measuring device; and
  (C) an elongate sensor cable comprising (1) a trunk line cable which follows an elongate trunk path having a near end and a far end; and (2) at least one branch line cable which extends from the trunk line cable at an intermediate point along the trunk path and follows an elongate branch path from the intermediate point to a distant point;

the trunk line cable comprising first, second, third and fourth elongate electrically conductive members which, at least in the absence of an event, are insulated from each other along the length of the trunk line cable, the first and second members being wires having a coating thereon of a conductive polymer composition which comprises a polymeric component and, dispersed in the polymeric component, a particulate conductive filler, the third and fourth members being insulated wires, and the first and second members being such that, upon occurrence of an event at a location along the trunk path, the first and second members become electrically connected at that location;

the branch line cable comprising fifth, sixth, seventh and eighth elongate electrically conductive members which, in the absence of an event, are insulated from each other along the length of the branch line cable, the fifth and sixth members being wires having a coating thereon of a conductive polymer composition which comprises a polymeric component and, dispersed in the polymeric component, a particulate conductive filler, the seventh and eighth members being insulated wires, and the fifth and sixth members being such that, upon occurrence of an event at a location along the branch path, the fifth and sixth members become electrically connected at that location;

the first member being electrically connected (a) at the near end of the trunk path, to the power source and to the voltage-measuring device, and (b) at the far end of the trunk path, to the third member;

the third member being electrically connected (a) at the near end of the trunk path, to the voltage-measuring device, and (b) at the far end of the trunk path, to the first member;

the fourth member being electrically connected (a) at the near end of the trunk path, to the power source, and (b) at the far end of the trunk path, to the second member;

the first and second members being discontinuous at the intermediate point so that each has an incoming end nearer the near end of the trunk path and an outgoing end nearer the far end of the trunk path;

each of the fifth, sixth, seventh and eighth members being connected at the intermediate point to one of the incoming and outgoing ends of the first and second members, and the fifth member being connected at the distant point of the branch line cable to the seventh or eighth member, and the sixth member being connected at the distant point of the branch line cable to the eighth member if the fifth member is connected to the seventh member and to the seventh member if the fifth member is connected to the eighth member, so that the incoming and outgoing ends of the first member are electrically connected to each other through the branch line, the incoming and outgoing ends of the second member are electrically connected to each other through the branch line cable, and, in the absence of an event, the first and second members are insulated from each other along the length of the sensor cable;

the second member and the members of the branch line cable connected between the incoming and outgoing ends of the second member together forming a source member;

the first member and the members of the branch line cable connected between the incoming and outgoing ends of the first member together forming a locating member which is insulated from the source member along the length of the sensor cable in the absence of an event but which, upon occurrence of an event, becomes electrically connected to the source member at a connection point, which has an impedance $T_{total}$ between the near end and the far end of the trunk path, and whose impedance between the near end of the trunk path and any point on the locating member to which the source member can be connected upon occurrence of an event is characteristic of the event;

the apparatus being such that, when an event causes the locating member and the source member to become electrically connected to each other at a connection point, the apparatus comprises a test circuit and a reference circuit, the test circuit being one in which a current of known size flows and which comprises (a) that part of the locating member which lies between the near end of the trunk path and the connection point, (b) the connection, (c) that part of the source member which lies between the connection point and the far end of the trunk path, said part of the source member having an impedance which is substantially equal to the difference between $T_{total}$ and the impedance of said part (a), (d) the fourth member of the trunk cable, and (e) the power source, and the reference circuit being one which comprises (a) the locating member, (b) the third member, and (c) the voltage-measuring device;

whereby the voltage measured by the voltage-measuring device can be used to determine the location of the connection point.

11. Apparatus according to claim 10 wherein the physical construction of the trunk cable is substantially identical to the physical construction of the branch cable.

12. Apparatus according to claim 10 wherein the fifth member is connected, at the intermediate point, to the incoming end of the first member, and the sixth member is connected, at the intermediate point, to the incoming end of the second member.

13. Apparatus according to claim 10 wherein the first, second, fifth and sixth members are substantially identical in physical construction.

14. Apparatus according to claim 13 wherein the third, fourth, seventh and eighth members are substantially identical in physical construction.

15. Apparatus according to claim 10 wherein a resistor is connected between each of the connections between the incoming and outgoing ends of the first and second members and the members of the branch cable to which they are respectively connected, the resistors being substantially identical.

16. Apparatus according to claim 15 in which the trunk and branch cables are comprised of preterminated lengths of cable which are joined together by sealed connection units and which are terminated by sealed termination units, the terminations of the preterminated cables and in the connection and termination units being such that they can only be connected in an electrically correct arrangement.

* * * * *

UNITED STATES PATENT AND TRADEMARK OFFICE
CERTIFICATE OF CORRECTION

PATENT NO. : 4,843,327

DATED : June 27, 1989

INVENTOR(S) : Koppitsch, et al

It is certified that error appears in the above-identified patent and that said Letters Patent is hereby corrected as shown below:

Column 8, line 19    Replace "$T_{total}$" by --$Z_{total}$--

Column 10, line 15   Replace "$T_{total}$" by --$Z_{total}$--

Column 10, line 37   Replace "$T_{total}$" by --$Z_{total}$--

Signed and Sealed this

First Day of January, 1991

*Attest:*

HARRY F. MANBECK, JR.

*Attesting Officer*     *Commissioner of Patents and Trademarks*